US010420713B2

(12) United States Patent
Grasl et al.

(10) Patent No.: US 10,420,713 B2
(45) Date of Patent: Sep. 24, 2019

(54) PATCH, SET OF PATCHES, METHOD AND USE FOR MEDICAL OR COSMETIC TREATMENT

(71) Applicants: Jürgen Grasl, Altmünster (AT); Dietmar Kowarik, Vienna (AT)

(72) Inventors: Jürgen Grasl, Altmünster (AT); Dietmar Kowarik, Vienna (AT)

( * ) Notice: Subject to any disclaimer, the term of this patent is extended or adjusted under 35 U.S.C. 154(b) by 0 days.

(21) Appl. No.: 15/304,284

(22) PCT Filed: Apr. 16, 2015

(86) PCT No.: PCT/EP2015/058294
§ 371 (c)(1),
(2) Date: Oct. 14, 2016

(87) PCT Pub. No.: WO2015/158841
PCT Pub. Date: Oct. 22, 2015

(65) Prior Publication Data
US 2017/0042772 A1    Feb. 16, 2017

Related U.S. Application Data

(60) Provisional application No. 61/980,688, filed on Apr. 17, 2014.

(51) Int. Cl.
*A61K 8/02* (2006.01)
*A61K 8/39* (2006.01)
*A61K 8/42* (2006.01)
*A61K 8/97* (2017.01)
*A61Q 19/00* (2006.01)

(52) U.S. Cl.
CPC .............. *A61K 8/0208* (2013.01); *A61K 8/39* (2013.01); *A61K 8/42* (2013.01); *A61K 8/97* (2013.01); *A61Q 19/00* (2013.01); *A61K 2800/88* (2013.01)

(58) Field of Classification Search
CPC .... A61K 2800/88; A61K 8/0208; A61K 8/39; A61K 8/42; A61K 8/97; A61Q 19/00
See application file for complete search history.

(56) References Cited

U.S. PATENT DOCUMENTS

| 2004/0109831 A1* | 6/2004 | Dodwell | A61K 8/29 424/59 |
| 2006/0029654 A1* | 2/2006 | Cassel | A61K 9/7061 424/449 |
| 2014/0200196 A1* | 7/2014 | Barrows | A61K 31/734 514/54 |

FOREIGN PATENT DOCUMENTS

| DE | 19708674 A1 | 10/1997 |
| DE | 19708674 C2 | 10/1997 |
| DE | 10330960 B4 | 2/2005 |
| EP | 10334918 A1 | 6/2005 |
| EP | 1289487 B1 | 12/2006 |
| WO | 2001002478 A1 | 1/2001 |
| WO | 2001078678 A1 | 10/2001 |
| WO | 2009124578 A2 | 10/2009 |
| WO | 2014145714 A1 | 9/2014 |

OTHER PUBLICATIONS

Press release from Wildcat Deutschland GmbH, Stutzmann, C, Revolutionary Protection for freshly tattooed tattoos, Presse Anzeiger, Jul. 7, 2009, English translation supplied, Last accessed on Mar. 21, 2013.
Bell International Laboratories, Material Safety Data Sheet Tattoo Innovations, Tattoo Hydrogel, Apr. 9, 2014, XP002739998, Retrieved from the Internet: URL: http://www.luckysupply.com/amfilerating/file/download/file_id/43/ (retrieved on May 21, 2015).
Bell International Laboratories, Material Safety Data Sheet Tattoo Innovations, Tattoo Sealant, Apr. 9, 2014, XP002739999, Retrieved from the Internet: URL: http://www.luckysupply.com/amfilerating/file/download/file_id/44/ (retrieved on May 21, 2015).
Representative screenshots (5 pages) of a Youtbue video retrieved on Jan. 10, 2017, video posted on Mar. 5, 2013 by Nelasertattooremoval, "SkinLock Hydrogel Applied to Fresh Tattoo"—4 mins. 15 secs. Full length video found at URL: https://www.youtube.com/watch?v=kB4Q1FKkPS8.
International Search Report dated Jun. 22, 2015 from related application PCT/EP20145/058294.

\* cited by examiner

*Primary Examiner* — Michael B. Pallay
(74) *Attorney, Agent, or Firm* — Larson & Anderson, LLC

(57) ABSTRACT

The invention relates to two different patches to be applied to a person's skin, namely a hydrogel patch and a dermal patch. The patches are preferably used in combination. A particularly preferred use of the patches is the post-treatment after tattooing. The patches' ingredients do not interact with the pigments used for tattooing and therefore the patches allow maintaining the color saturation of a tattoo.

15 Claims, No Drawings

PATCH, SET OF PATCHES, METHOD AND USE FOR MEDICAL OR COSMETIC TREATMENT

The present invention relates to two different patches to be applied to a person's skin, namely a hydrogel patch and a dermal patch. The patches are preferably used in combination. A particularly preferred use of the patches is the post-treatment after tattooing. The patches' ingredients do not interact with the pigments used for tattooing and therefore the patches allow maintaining the color saturation of a tattoo.

The invention further relates to the use of the patches and to a method of treatment employing the patches, either individually or, preferably, in combination for medical or cosmetic (i.e. non-medical) treatment. Cosmetic treatment, in particular the afore-mentioned post-treatment after tattooing is preferred.

BACKGROUND ART

Hydrogel patches and dermal patches (including transdermal patches; TTS patches) are well known in the art. Examples are known from WO 2009/124578 A2, DE 19708674 C2, and EP 1289487 B1.

DESCRIPTION OF THE INVENTION

The present invention relates to patches, to their use and to methods of treatment employing the patches.

In the present invention, the term "patch" is used in a broad sense and generally encompasses but is not limited to a skin dressing, a wound dressing, and a patch in strict sense. For the sake of brevity, the term "patch" is used in the present application, although all definitions mentioned above equally apply.

Numeric ranges recited in the present invention may be combined in any reasonable way. Specifically, if multiple upper limits and multiple lower limits of a range (including the broadest disclosed range) are disclosed, it is intended to cover each range obtained by combining any upper limit with any lower limit. It is even desired to cover any combination of lower limits and/or upper limits.

Further, if not stated otherwise, "%" in the present invention means "wt.-%" (% by weight). Moreover, whenever the description below states that an ingredient is contained in a certain amount (wt.-%) in a material, this means that the percentage is relative to the total (weight) of the material. For example, the statement below that the "hydrogel sheet contains at least 40.00 wt.-% water" means that the "hydrogel sheet contains at least 40.00 wt.-% water when assuming that the total weight of the hydrogel sheet is 100 wt.-%".

In the present invention, ingredients will sometimes be referred to in accordance with the INCI/CTFA nomenclature (International Nomenclature of Cosmetic Ingredients). In any case, if an acidic or basic ingredient is disclosed below, it is desired to include the acidic or basic from, respectively, as well as pharmacologically and/or cosmetically acceptable salts thereof either individually or as a mixture. Similarly, if the description below recites a salt, it is desired to include the salt form as well as the free acid/base form thereof either individually or as a mixture.

The present invention is described by the following items and the subsequent detailed description, which describes the invention in general as well as preferred embodiments of the invention. In the following, embodiments of the present invention will be explained. Each of these embodiments may be combined, either individually or in combination, with each of the items above, if not explicitly stated otherwise. It should be noted that the present invention is not restricted to these specific embodiments but also encompass modifications and/or equivalents to these embodiments being easily recognizable for the person skilled in the art.

Item 1. A set of patches including a hydrogel patch and a dermal patch, wherein the hydrogel patch comprises a hydrogel sheet and preferably a support sheet; and the dermal patch comprises an active sheet and preferably a support sheet.

Item 2. A dermal patch comprising an active sheet and preferably a support sheet, wherein the active sheet contains at least a polymeric binder, an emulsifier, panthenol, aloe barbadensis leaf extract, and a surfactant.

Item 3. A hydrogel patch comprising a hydrogel sheet and preferably a support sheet, wherein the hydrogel sheet contains at least water, a gelling agent, a thickener, an emulsifier, a preservative and/or a moisturizer, panthenol, and aloe barbadensis leaf extract.

Item 4. The hydrogel patch according to item 3 for use in combination with a dermal patch, preferably in combination with the dermal patch according to item 2.

Item 5. The dermal patch according to item 2 for use in combination with a hydrogel patch, preferably in combination with the hydrogel patch according to item 3.

Item 6. The set of patches according to item 1, wherein the hydrogel sheet contains at least water, a gelling agent, a thickener, an emulsifier, a preservative and/or a moisturizer, panthenol, and aloe barbadensis leaf extract.

Item 7. The set of patches or the hydrogel patch according to any one of items 3 to 6, wherein the hydrogel sheet contains
at least 40.00 wt.-% water,
6.50-39.00 wt.-% gelling agent,
5.00-20.00 wt.-% thickener,
0.50-10.00 wt.-% emulsifier,
0.50-10.00 wt.-% moisturizer,
0.06-10.00 wt.-% preservative,
0.05-10.00 wt.-% panthenol, and
0.05-10.00 wt.-% aloe barbadensis leaf extract.

Item 8. The set of patches or the hydrogel patch according to any one of items 3 to 7, wherein the gelling agent is selected from algin (sodium alginate), pectin, carrageen, gelatine, galactomannane, dextrane, and cellulose gum.

Item 9. The set of patches or the hydrogel patch according to any one of items 3 to 8, wherein the gelling agent is a mixture of gelling agents, preferably a mixture of cellulose gum and at least one of algin, pectin, carrageen, gelatine, galactomannane, and dextrane, more preferably mixture of cellulose gum and algin.

Item 10. The set of patches or the hydrogel patch according to any one of items 3 to 9, wherein the hydrogel sheet contains 6.00-20.00 wt.-%, more preferably 8.00-16.00 wt.-%, more preferably 10.00-14.00 wt.-%, more preferably 11.60-12.40 wt.-% of a first gelling agent, preferably of algin as a gelling agent.

Item 11. The set of patches or the hydrogel patch according to any one of items 3 to 10, wherein the hydrogel sheet contains 0.50-19.00 wt.-%, more preferably 1.00-6.00 wt.-%, more preferably 1.50-4.00 wt.-%, more preferably 1.60-2.40 wt.-% of a second gelling agent, preferably of cellulose gum as a gelling agent.

Item 12. The set of patches or the hydrogel patch according to any one of items 3 to 11, wherein the thickener is polyvinyl alcohol.

Item 13. The set of patches or the hydrogel patch according to any one of items 3 to 12, wherein the hydrogel sheet contains 5.00-20.00 wt.-%, more preferably 7.00-16.00 wt.-%, more preferably 9.00-13.00 wt.-%, more preferably 10.55-11.40 wt.-% thickener.

Item 14. The set of patches or the hydrogel patch according to any one of items 3 to 13, wherein the emulsifier is laureth-9 (polidocanol).

Item 15. The set of patches or the hydrogel patch according to any one of items 3 to 14, wherein the hydrogel sheet contains 0.50-10.00 wt.-%, more preferably 1.00-7.00 wt.-%, more preferably 2.00-5.00 wt.-%, more preferably 2.60-3.40 wt.-% emulsifier.

Item 16. The set of patches or the hydrogel patch according to any one of items 3 to 15, wherein the moisturizer is pentylene glycol.

Item 17. The set of patches or the hydrogel patch according to any one of items 3 to 16, wherein the hydrogel sheet contains 0.50-10.00 wt.-%, more preferably 1.00-7.00 wt.-%, more preferably 2.00-5.00 wt.-%, more preferably 2.60-3.40 wt.-% moisturizer.

Item 18. The set of patches or the hydrogel patch according to any one of items 3 to 17, wherein the preservative is one or both of phenoxyethanol and ethylhexylglycerin.

Item 19. The set of patches or the hydrogel patch according to any one of items 3 to 18, wherein the hydrogel sheet contains 0.05-5.00 wt.-%, more preferably 0.10-4.00 wt.-%, more preferably 0.50-3.00 wt.-%, more preferably 0.60-0.90 wt.-% of a first preservative, preferably of phenoxyethanol as a preservative.

Item 20. The set of patches or the hydrogel patch according to any one of items 3 to 19, wherein the hydrogel sheet contains 0.01-5.00 wt.-%, more preferably 0.03-1.50 wt.-%, more preferably 0.05-0.70 wt.-%, more preferably 0.06-0.20 wt.-% of a second preservative, preferably of ethylhexylglycerin as a preservative.

Item 21. The set of patches or the hydrogel patch according to any one of items 3 to 20, wherein the hydrogel sheet contains at least water, algin, polyvinyl alcohol, laureth-9 (polyethylene glycol-9 lauryl alcohol, polidocanol), pentylene glycol, cellulose gum (carboxymethyl cellulose), panthenol (2,4-Dihydroxy-N-(3-hydroxypropyl)-3,3-dimethylbutanamide), aloe barbadensis leaf extract, phenoxyethanol, and ethylhexylglycerin (3-[(2-ethylhexyl)oxy]-1,2-propanediol).

Item 22. The set of patches according to embodiments herein described, wherein the active sheet contains at least a polymeric binder, an emulsifier, panthenol, aloe barbadensis leaf extract, and a surfactant.

Item 23. The set of patches or the dermal patch according to any one of items 2 and 4 to 22, wherein said active sheet contains
at least 50.00 wt.-% polymeric binder,
0.50-10.00 wt.-% emulsifier,
0.05-10.00 wt.-% panthenol,
0.05-10.00 wt.-% aloe barbadensis leaf extract, and
0.05-5.00 wt.-% surfactant.

Item 24. The set of patches or the dermal patch according to any one of items 2 and 4 to 23, wherein said polymeric binder is a cosmetically acceptable copolymer binder, preferably acrylates copolymer or a mixture comprising acrylates copolymer.

Item 25. The set of patches or the dermal patch according to any one of items 2 and 4 to 24, wherein active sheet contains at least 50.00 wt.-%, preferably 65.00-95.00 wt.-%, more preferably 80.00-93.00 wt.-% polymeric binder.

Item 26. The set of patches or the dermal patch according to any one of items 2 and 4 to 25, wherein the emulsifier is laureth-9 (polidocanol).

Item 27. The set of patches or the dermal patch according to any one of items 2 and 4 to 26, wherein the active sheet contains 0.50-10.00 wt.-%, more preferably 1.00-7.00 wt.-%, more preferably 2.00-5.00 wt.-%, more preferably 2.60-3.40 wt.-% emulsifier.

Item 28. The set of patches or the dermal patch according to any one of items 2 and 4 to 27, wherein the surfactant is a polysorbate surfactant, preferably polysorbate 80.

Item 29. The set of patches or the dermal patch according to any one of items 2 and 4 to 28, wherein the hydrogel sheet contains 0.05-5.00 wt.-%, more preferably 0.20-4.00 wt.-%, more preferably 2.00-5.00 wt.-%, more preferably 2.60-3.40 wt.-% surfactant.

Item 30. The set of patches or the dermal patch according to any one of items 2 and 4 to 29, wherein the active sheet contains at least acrylates copolymer, laureth-9 (polidocanol), panthenol, aloe barbadensis leaf extract, and polysorbate 80.

Item 31. The set of patches or the hydrogel patch according to any one of items 1 and 3 to 30, wherein said hydrogel sheet contains
at least 40.00 wt.-% water,
6.00-20.00 wt.-% algin,
5.00-20.00 wt.-% polyvinyl alcohol,
0.50-10.00 wt.-% laureth-9 (polidocanol),
0.50-10.00 wt.-% pentylene glycol,
0.50-19.00 wt.-% cellulose gum,
0.05-10.00 wt.-% panthenol,
0.05-10.00 wt.-% aloe barbadensis leaf extract,
0.05-5.00 wt.-% phenoxyethanol, and
0.01-5.00 wt.-% ethylhexylglycerin.

Item 32. The set of patches or the hydrogel patch according to any one of items 1 and 3 to 31, wherein said hydrogel sheet contains at least 50.00 wt.-% water, preferably at least 60.00 wt.-% water, preferably at most 85.00 wt.-% water, more preferably at most 80.00 wt.-% water.

Item 33. The set of patches or the hydrogel patch according to any one of items 1 and 3 to 32, wherein said hydrogel sheet contains at least 8.00 wt.-% algin, preferably at least 10.00 wt.-% algin, preferably at most 16.00 wt.-% algin, more preferably at most 14.00 wt.-% algin, more preferably 11.60-12.40 wt.-% algin.

Item 34. The set of patches or the hydrogel patch according to any one of items 1 and 3 to 33, wherein said hydrogel sheet contains at least 7.00 wt.-% polyvinyl alcohol, preferably at least 9.00 wt.-% polyvinyl alcohol, preferably at most 16.00 wt.-% polyvinyl alcohol, more preferably at most 13.00 wt.-% polyvinyl alcohol, most preferably 10.55-11.40 wt.-% polyvinyl alcohol.

Item 35. The set of patches or the hydrogel patch according to any one of items 1 and 3 to 34, wherein said hydrogel sheet contains at least 1.00 wt.-% laureth-9 (polidocanol), preferably at least 2.00 wt.-% laureth-9 (polidocanol), preferably at most 7.00 wt.-% laureth-9 (polidocanol), more preferably at most 5.00 wt.-% laureth-9 (polidocanol), most preferably 2.60-3.40 wt.-% laureth-9 (polidocanol).

Item 36. The set of patches or the hydrogel patch according to any one of items 1 and 3 to 35, wherein said hydrogel sheet contains at least 1.00 wt.-% laureth-9 (polidocanol), preferably at least 2.00 wt.-% laureth-9 (polidocanol), preferably at most 7.00 wt.-% laureth-9 (polidocanol), more preferably at most 5.00 wt.-% laureth-9 (polidocanol), most preferably 2.60-3.40 wt.-% laureth-9 (polidocanol).

Item 37. The set of patches or the hydrogel patch according to any one of items 1 and 3 to 36, wherein said hydrogel sheet contains at least 1.00 wt.-% pentylene glycol, preferably at least 1.60 wt.-% pentylene glycol, preferably at most 6.00 wt.-% pentylene glycol, more preferably at most 54.00 wt.-% pentylene glycol, most preferably 2.00-2.90 wt.-% pentylene glycol.

Item 38. The set of patches or the hydrogel patch according to any one of items 1 and 3 to 37, wherein said hydrogel sheet contains at least 1.00 wt.-% cellulose gum, preferably at least 1.50 wt.-% cellulose gum, preferably at most 6.00 wt.-% cellulose gum, more preferably at most 4.00 wt.-% cellulose gum, most preferably 1.60-2.40 wt.-% cellulose gum.

Item 39. The set of patches or the hydrogel patch according to any one of items 1 and 3 to 38, wherein said hydrogel sheet contains at least 0.10 wt.-% panthenol, preferably at least 0.50 wt.-% panthenol, preferably at most 5.00 wt.-% panthenol, more preferably at most 3.00 wt.-% panthenol, most preferably 0.80-1.30 wt.-% panthenol.

Item 40. The set of patches or the hydrogel patch according to any one of items 1 and 3 to 39, wherein said hydrogel sheet contains at least 0.10 wt.-% aloe barbadensis leaf extract, preferably at least 0.50 wt.-% aloe barbadensis leaf extract, preferably at most 5.00 wt.-% aloe barbadensis leaf extract, more preferably at most 3.00 wt.-% aloe barbadensis leaf extract, most preferably 0.80-1.30 wt.-% aloe barbadensis leaf extract.

Item 41. The set of patches or the hydrogel patch according to any one of items 1 and 3 to 40, wherein said hydrogel sheet contains at least 0.10 wt.-% phenoxyethanol, preferably at least 0.50 wt.-% phenoxyethanol, preferably at most 4.00 wt.-% phenoxyethanol, more preferably at most 3.00 wt.-% phenoxyethanol, most preferably 0.60-0.90 wt.-% phenoxyethanol.

Item 42. The set of patches or the hydrogel patch according to any one of items 1 and 3 to 41, wherein said hydrogel sheet contains at least 0.03 wt.-% ethylhexylglycerin, preferably at least 0.05 wt.-% ethylhexylglycerin, preferably at most 1.50 wt.-% ethylhexylglycerin, more preferably at most 0.70 wt.-% ethylhexylglycerin, most preferably 0.06-0.20 wt.-% ethylhexylglycerin.

Item 43. The set of patches or the hydrogel patch according to any one of items 1 and 3 to 42, wherein said hydrogel sheet is formed of a plurality of individual sheets.

Item 44. The set of patches or the hydrogel patch according to any one of items 1 and 3 to 43, wherein said hydrogel sheet is formed of a single sheet.

Item 45. The set of patches or the hydrogel patch according to any one of items 1 and 3 to 44, wherein said hydrogel patch further comprises a protective sheet.

Item 46. The set of patches or the hydrogel patch according to item 45, wherein said hydrogel sheet is sandwiched between said support sheet and said protective sheet.

Item 47. The set of patches or the dermal patch according to any one of items 1, 2 and 4 to 46, wherein said active sheet contains
at least 50.00 wt.-% acrylates copolymer,
0.50-10.00 wt.-% laureth-9 (polidocanol),
0.05-10.00 wt.-% panthenol,
0.05-10.00 wt.-% aloe barbadensis leaf extract, and
0.05-5.00 wt.-% polysorbate 80.

Item 48. The set of patches or the dermal patch according to any one of items 1, 2 and 4 to 47, wherein said active sheet contains at least 65.00 wt.-% acrylates copolymer, preferably at least 80.00 wt.-% acrylates copolymer, preferably at most 95.00 wt.-% acrylates copolymer, more preferably at most 93.00 wt.-% acrylates copolymer.

Item 49. The set of patches or the dermal patch according to any one of items 1, 2 and 4 to 48, wherein said active sheet contains at least 1.00 wt.-% laureth-9 (polidocanol), preferably at least 2.00 wt.-% laureth-9 (polidocanol), preferably at most 7.00 wt.-% laureth-9 (polidocanol), more preferably at most 5.00 wt.-% laureth-9 (polidocanol), most preferably 2.60-3.40 wt.-% laureth-9 (polidocanol).

Item 50. The set of patches or the dermal patch according to any one of items 1, 2 and 4 to 49, wherein said active sheet contains at least 0.20 wt.-% panthenol, preferably at least 0.70 wt.-% panthenol, preferably at most 5.00 wt.-% panthenol, more preferably at most 3.00 wt.-% panthenol, most preferably 1.10-1.60 wt.-% panthenol.

Item 51. The set of patches or the dermal patch according to any one of items 1, 2 and 4 to 50, wherein said active sheet contains at least 0.20 wt.-% aloe barbadensis leaf extract, preferably at least 0.70 wt.-% aloe barbadensis leaf extract, preferably at most 5.00 wt.-% aloe barbadensis leaf extract, more preferably at most 3.00 wt.-% aloe barbadensis leaf extract, most preferably 1.10-1.60 wt.-% aloe barbadensis leaf extract.

Item 52. The set of patches or the dermal patch according to any one of items 1, 2 and 4 to 51, wherein said active sheet contains at least 0.20 wt.-% polysorbate 80, preferably at least 0.70 wt.-% polysorbate 80, preferably at most 4.00 wt.-% polysorbate 80, more preferably at most 3.00 wt.-% polysorbate 80, most preferably 1.10-1.60 wt.-% polysorbate 80.

Item 53. The set of patches or the dermal patch according to any one of items 1, 2 and 4 to 52, wherein said active sheet is formed of a plurality of individual sheets.

Item 54. The set of patches or the dermal patch according to any one of items 1, 2 and 4 to 53, wherein said active sheet is formed of a single sheet.

Item 55. The set of patches or the dermal patch according to any one of items 1, 2 and 4 to 54, wherein said dermal patch further comprises a protective sheet.

Item 56. The set of patches or the dermal patch according to item 55, wherein said active sheet is sandwiched between said support sheet and said protective sheet.

Item 57. The set of patches or the dermal patch according to any one of items 1, 2 and 4 to 56, wherein said active sheet further contains a modifier, preferably in an amount of at least 0.01 wt.-% and preferably in an amount of at most 15.00 wt.-%.

Item 58. The set of patches or the hydrogel patch according to any one of items 1 and 3 to 57, wherein said hydrogel sheet further contains a modifier, preferably in an amount of at least 0.01 wt.-% and preferably in an amount of at most 15.00 wt.-%.

Item 59. The set of patches, the hydrogel patch or the dermal patch according to item 57 or 58, wherein said modifier is contained in an amount of at least 0.10 wt.-%, preferably in an amount of at most 5.00 wt.-%.

Item 60. The set of patches, the hydrogel patch or the dermal patch according to any one of items 57 to 59, wherein said modifier comprises at least one of local (topical) anesthetics, preferably lidocaine-like local (topical) anesthetics such as lidocaine, tetracine, prilocaine, and benzocaine and/or hydrochlorides and derivates thereof.

Item 61. The set of patches, the hydrogel patch or the dermal patch according to any one of items 57 to 60, wherein said modifier comprises a skin care agent or a skin curative agent such as allantoin, hamamelis virginiana extract, vitamin E, vitamin A, centella asiatica extract, matricaria chamomilla extract, arnica montana extract, salvia officinalis extract, symphytum officinale extract, Na-hyalonurat, coenzyme Q 10, or alpha-liponic acid.

Item 62. The set of patches, the hydrogel patch or the dermal patch according to any one of items 57 to 61, wherein said modifier comprises a fat, an oil or an essential oil such as olive oil, evening primrose oil, (sweet) almond oil, essential lavender oil, or oils or fat comprising omega-3 fatty acids.

Item 63. The set of patches, the hydrogel patch or the dermal patch according to any one of items 57 to 62, wherein said modifier comprises a skin cooling agent such as menthol, camphor, or essential peppermint oil.

Item 64. The set of patches, the hydrogel patch or the dermal patch according to any one of items 57 to 63, wherein said modifier comprises a disinfectant such as a salt of chorhexidine, e.g. chlorhexidine digluconate.

Item 65. The set of patches, the hydrogel patch or the dermal patch according to any one of items 57 to 64, wherein said modifier comprises a sun protection agent or a UV filter, such as titanium oxide or other micro-pigments or nano-pigments.

Item 66. The set of patches, the hydrogel patch or the dermal patch according to any one of items 57 to 65, wherein said modifier comprises a bleaching agent such as liquirtia extract, kojic acid, arbutin, Chromabright® or Melfade®, and wherein said set of patches, hydrogel patch or dermal patch is not for post-treatment after tattooing.

Item 67. Use of the dermal patch according to any one of items 5, 23 to 30, 47 to 57, and 59 to 66 in combination with a hydrogel patch for improving the skin appearance after tattooing.

Item 68. Use of the set of patches according to any one of items 1 and 6 to 65 for improving the skin appearance after tattooing.

Item 69. Use of the hydrogel patch according to any one of items 3, 4, 7 to 21, 31 to 46, and 58 to 66 in combination with a dermal patch for improving the skin appearance after tattooing.

Item 70. The use according to any one of items 67 or 69, wherein the hydrogel patch is applied first and then the dermal patch is applied (to the same skin region) after the hydrogel patch is removed.

Item 71. A set of patches, a dermal patch or a hydrogel patch as defined in any one of items 1 to 66 for use in the prevention or treatment of a disease or a malfunction of the body.

Item 72. A set of patches, a dermal patch or a hydrogel patch as defined in any one of items 1 to 66 for cosmetic use and/or for use in cosmetic treatment.

Item 73. The set of patches for use according to item 71 or 72, wherein the use comprises applying the hydrogel patch to a person's skin, then removing the hydrogel patch after 5 minutes to 24 hours, and then applying the dermal patch to the person's skin approximately at the same position where the hydrogel patch was applied.

Item 74. The set of patches for use according to any one of items 71 to 73, wherein the use comprises applying the hydrogel patch to a part of a person's skin on which a tattoo has been formed within 10 minutes after said tattoo has been formed.

Item 75. A method of cosmetically treating a person's skin after tattooing, the method comprising applying a dermal patch to part of a person's skin on which a tattoo has been formed, wherein the dermal patch is the dermal patch according to any one of items 5, 23 to 30, 47 to 57, and 59 to 66.

Item 76. A method of cosmetically treating a person's skin after tattooing, the method comprising applying a hydrogel patch to part of a person's skin on which a tattoo has been formed, wherein the hydrogel patch is the hydrogel patch according to any one of items 3, 4, 7 to 21, 31 to 46, and 58 to 66.

Item 77. A method of cosmetically treating a person's skin after tattooing, the method comprising applying a hydrogel patch to part of the person's skin on which a tattoo has been formed, removing the hydrogel patch, and then applying a dermal patch to said part of the person's skin, wherein the hydrogel patch is the hydrogel patch according to any one of items 3, 4, 7 to 21, 31 to 46, and 58 to 66 and the dermal patch is the dermal patch according to any one of items 5, 23 to 30, 47 to 57, and 59 to 66, or the hydrogel patch and the dermal patch are a set of patches according to any one of items 1 and 6 to 66.

Item 78. The method according to item 76 or 77, wherein the hydrogel patch is removed 5 minutes to 24 hours after applying it to the person's skin.

Item 79. The method according to item 77 or 78, wherein the dermal patch is applied within 20 minutes, preferably within 10 minutes, more preferably within 5 minutes, after removing the hydrogel patch.

Item 80. The method according to any one of items 76 to 79, wherein the hydrogel patch is applied to said part of the person's skin on which said tattoo has been formed within 10 minutes after said tattoo has been formed.

The patch(es) and the set of patches as defined in the forgoing items can be applied in the uses as defined in the accompanying claims as well as the more general defined method and uses of the invention, unless they are explicitly excluded for the respective uses (see e.g. item 66).

In the following, further embodiments and benefits of the present invention will be explained. Each of these preferred embodiments may be combined, either individually or in combination, with each of the items above, if not explicitly stated otherwise.

The present invention is particularly useful for treating the skin after tattooing (preferably applying the patch(es) within 15 minutes after tattooing has been finished). In particular, the hydrogel patch may be applied to a freshly tattooed skin portion and achieves immediate cooling of the skin portion. Thus, the skin irritation caused by tattooing can be alleviated and the appearance of the skin can be improved. Further, the hydrogel patch can absorb excessive fluids (e.g. wound oozing) and protect the skin from mechanical injury and/or UV radiation. Accordingly, the hydrogel patch may prevent or alleviate the occurrence of itching, reddened skin, rash and burning sensation.

Without wanting to be bound to theory, it is assumed that the cooling action and the protective action prevents the color (pigments) of the tattoo from being expelled from the freshly tattooed skin. Thus, it is assumed that the color protection and color improvement is at least partially due to skin soothing and protection against mechanical and UV stress.

Preferably, the dermal patch of the present invention is applied to approximately the same region of a person's skin from which the hydrogel patch has been removed. The dermal patch may thus protect the skin from mechanical injury and/or UV radiation and may prevent or alleviate the occurrence of itching, reddened skin, rash and burning sensation. Furthermore, since the dermal patch shows higher wearing comfort, better customer compliance may be expected and it is more likely that the patch is applied for a sufficient period of time so as to secure the color improvement.

The patch, patches or set of patches (in the following: patch) may be used for post-treatment (immediately, e.g. within the first 3 hours) after tattooing. The patch may also be used for cosmetic or medical treatment on tattooed skin portions after the skin irritations caused by tattooing are not detectable any more (treatment other than post-treatment after tattooing). In both cases, the patch most preferably does not contain an ingredient deteriorating the color appearance of the tattoo. That is, the patch preferably does not contain an ingredient or ingredients interacting with the pigments or other colors used for tattooing.

In further preferred embodiments, the patch, patches or set of patches (in the following: patch) may be alternatively or additionally used for treating 1. Skin irritations due to allergic reactions (especially in case of redness, itching and for cooling the skin) or skin irritations due to contact with skin-irritating substances (especially acids, bases, substances causing irritations when coming into contact with the skin or hazardous substances);

2. Skin injuries (especially superficial burns; sunburn etc.) and radiation affections or injuries of the skin (especially after laser treatment, e.g. when removing tattoos by laser light), or due to radiation or exposure (e.g. ionizing radiation for treating cancer) UV radiation (during dermatologic treatments etc.);

3. All kinds of wounds and lesions (especially abrasion wounds, cuts or wounds resulting from operations).

According to preferred embodiments of the invention, the patch(es) may comprise at least one of the following modifiers (active ingredients).

Vulnerary, Anti-Inflammatory and Soothing Agents:

Bisabolol, Aloe vera/Aloe barbadensis (leaf) extract, dexpanthenol, vitamin E, Witch-hazel (Hamamelis) extract, Arnica extract, Salvia extract, Symphytum extract (fluid und alcoholic and solid), hyaluronic acid and their salts, ammonium bituminosulphonate, zinc oxide, vitamin A, cod liver (oil), blood hemolysates, essential lavender oil, tea-tree oil, olive oil, evening primrose oil, (sweet) almond oil, essential lavender oil, or oils or fat comprising omega-3 fatty acids, allantoin, propolis, medicinal honey.

Cooling Agents:

Essential mint oil, essential eucalyptus oil, menthol.

Analgetic Agents:

Polidocanol (also known as laureth-9), lidocain, tetracain, mepivacain, benzocain, prilocain, bupivacain and their hydrochlorides and pharmaceutical/cosmetic acceptable salts.

Preferably, the patch(es) (i.e. the dermal patch and/or the hydrogel patch) of the invention comprise at least (dex) panthenol, more preferably at least a combination of (dex) panthenol and aloe barbadensis (leaf) extract, and even more preferably at least a combination of (dex)panthenol, aloe barbadensis leaf extract and polidocanol. In a further preferred embodiment, the patch(es) (i.e. the dermal patch and/or the hydrogel patch) of the present invention comprises one of the following combinations: (dex)panthenol and aloe barbadensis (leaf) extract; (dex)panthenol and polidocanol; aloe barbadensis (leaf) extract and polidocanol; and (dex)panthenol, aloe barbadensis (leaf) extract and polidocanol.

Since the patch does not interact with the colors of the tattoo the post-treatment or the cosmetic or medical treatment other than post-treatment can be applied to a skin portion carrying a tattoo without concerning that the color of the tattoo could fade. Since such a constitution broadens the application range of a patch, this constitution (excluding ingredients interacting with the pigments or other colors used for tattooing) is preferable for any patch and any use or method of the present invention.

The hydrogel patch of the present invention may be self-supporting or may contain a hydrogel sheet provided on a support sheet, optionally comprising a further sheet or further sheets between the hydrogel sheet and the support sheet, and/or on the side of the support sheet opposing the hydrogel sheet. Preferably, the support sheet of the hydrogel patch is provided as a non-woven tissue.

The dermal patch of the present invention may be self-supporting or may contain an active sheet provided on a support sheet, optionally comprising a further sheet or further sheets between the active sheet and the support sheet, and/or on the side of the support sheet opposing the active sheet. Preferably, the support sheet of the active patch is provided as a polyurethane sheet. If the active sheet is the outermost sheet on at least one side of the patch (excluding an optional release liner), the active sheet is preferably an adhesive sheet or the active sheet is surrounded by an adhesive sheet on at least two sides so that the adhesive sheet and the active sheet form the outermost sheet.

The active sheet of the present invention is a sheet comprising an active ingredient, preferably a cosmetic active ingredient, such as panthenol (i.e. D-panthenol, also known as dexpanthenol) more preferably at least a combination of (dex)panthenol and aloe barbadensis (leaf) extract, and even more preferably a combination of (dex)panthenol, aloe barbadensis leaf extract and/or polidocanol. In a further preferred embodiment, the active sheet of the present invention comprises one of the following combinations: (dex) panthenol and aloe barbadensis (leaf) extract; (dex)panthenol and polidocanol; aloe barbadensis (leaf) extract and polidocanol; and (dex)panthenol, aloe barbadensis (leaf) extract and polidocanol.

A sheet of the present invention may be in the form of a continuous sheet or a discontinuous sheet.

The dermal patch of the present invention may be a patch for providing an active ingredient (cosmetic and/or medical active ingredient) into the skin only and/or through the skin into the blood stream (transdermal patch; TTS patch).

A set of patches of the present invention comprises two or more separate patches (including at least a hydrogel patch and a dermal patch) packed in a single package as well as two or more separate patches (including at least a hydrogel patch and a dermal patch) packed in two or more separate packages and designed and/or designated for combined use.

The patch of the present invention may have any shape and size. Commonly, the shape is rectangular, but may be circular, heart-shaped, star-shaped or any other shape. Typical sizes range from 2 cm×2 cm to 50 cm×100 cm.

Working embodiments of the hydrogel patch and of the dermal patch of present invention are described below. Again, these examples should not be interpreted as restricting the scope of the invention.

EXAMPLES

Example 1

Hydrogel Patch

A hydrogel patch was prepared by mixing a hydrogel ingredient composition to prepare a bulk mixture, applying the bulk mixture to a support liner and punching out a 5 cm×5 cm patch in a rectangular shape. The bulk mixture had the following composition:

| | |
|---|---|
| 12.00 wt.-% | ALGIN |
| 10.74 wt.-% | POLYVINYL ALCOHOL |
| 3.00 wt.-% | LAURETH-9 |
| 2.46 wt.-% | PENTYLENE GLYCOL |
| 1.94 wt.-% | CELLULOSE GUM |
| 1.00 wt.-% | PANTHENOL |
| 1.00 wt.-% | *ALOE BARBADENSIS* LEAF EXTRACT |
| 0.74 wt.-% | PHENOXYETHANOL |
| 0.08 wt.-% | ETHYLHEXYLGLYCERIN |
| Remainder (67.04 wt.-%) | AQUA (WATER) |

Example 2

Dermal Patch

A dermal patch was prepared by mixing an active ingredient composition to prepare a bulk mixture, applying the bulk mixture to a support liner and punching out a 5 cm×5 cm patch in a rectangular shape. The bulk mixture had the following composition:

| | |
|---|---|
| 3.00 wt.-% | LAURETH-9 |
| 1.35 wt.-% | PANTHENOL |
| 1.35 wt.-% | *ALOE BARBADENSIS* LEAF EXTRACT |
| 1.35 wt.-% | POLYSORBATE 80 |
| Remainder (92.95 wt.-%) | ACRYLATES COPOLYMER |

Example 3

Set of Patches

The hydrogel patch and the dermal patch of the working embodiment above were employed as a set of patches.

Example 4

Tests

The test patches were applied to different regions of a freshly formed tattoo. For comparison, a common patch (having no cooling action or active ingredient) was placed on a further region of the freshly formed tattoo.

The patches were removed after 10 hours. In the case of the set of patches, the hydrogel patch was removed after 1 hour, followed by immediate application of the dermal patch, and the dermal patch was removed after 9 more hours.

After 7 days, the tattoo was visually inspected. Besides improved healing of the skin at portions where the patches of the present invention have been applied, the color saturation was better in the regions where the patches of the present invention were applied. Best results regarding the color saturation could be achieved where the set of patches was applied, while good results were achieved where only the dermal patch or only the hydrogel patch was applied, wherein the hydrogel patch yielded better results out of these two.

Example 5

Tests

In addition to the above tests, two experts in the field of tattooing were asked to test the patches of the invention.

a) The first expert is a medic, who applied the dermal patch on a new tattoo immediately after finishing the tattooing. Compared to other tattoos, which were tattooed in parallel, at the site where the patch was applied significant advantages were observed by this expert:

1. No wound exudates were secreted.
2. There was no inflammation.
3. The color of the tattoo was more intense.
4. The wound healing was better and faster.
5. There was less pain.
6. The mechanical protection by the patch had a plurality of advantages (No rubbing in contact with clothes. No rubbing during sleep. Protection against external impacts. Protection when taking a shower. The time after tattooing was significantly more comfortable.)
7. There was less incrustation.
8. There was no interaction between the care/the active components and the tattoo colors.
9. Less care was necessary. (Creams or ointments need frequent application. The path was applied once.

All in all, the post-treatment/care with the patch was the best method this expert has ever tried.

b) The second expert is a Tattoo Artist who has won numerous awards.

The second expert reported that he personally has a lot of tattoos and tried a lot of different care products after tattooing. The second expert observed the following advantages with respect to a tattoo tattooed by this expert:

Better color, better wound healing, less side effects (pains, wound exudates, inflammation), good mechanical protection against external factors (e.g. rubbing, water), no interaction between the care/the active components and the used tattoo colors.

The invention claimed is:

1. A method for use of a dermal patch and/or a hydrogel patch for the post-treatment of skin after tattooing, comprising the step of applying the dermal patch and the hydrogel patch to skin after tattooing wherein the dermal patch and/or the hydrogel patch contains panthenol.

2. The method of claim 1, for improving the skin appearance after tattooing.

3. The method of claim 1, wherein the hydrogel patch is applied first and then the dermal patch is applied to the same skin region after the hydrogel patch is removed.

4. The method of claim 1, wherein the dermal patch and/or the hydrogel patch further contains at least one active agent, selected from the group consisting of vulnerary agents, anti-inflammatory agents, soothing agents, cooling agents and analgesic agents.

5. The method of claim 1, wherein the dermal patch and/or the hydrogel patch further contains at least one active agent, selected from allantoin, hamamelis virginiana extract, vitamin E, vitamin A, centella asiatica extract, matricaria chamomilla extract, arnica montana extract, salvia officinalis extract, symphytum officinale extract, Na-hyalonurat, coenzyme Q 10, or alpha-liponic acid, bisabolol, aloe vera/aloe barbadensis extract, vitamin E, hyaluronic acid and their salts, ammonium bituminosulphonate, zinc oxide, vitamin A, cod liver, blood hemolysates, essential lavender oil, tea-tree oil, olive oil, evening primrose oil, almond oil, essential lavender oil, or oils or fat comprising omega-3 fatty acids, propolis, medicinal honey, essential mint oils, essential eucalyptus oil, menthol, camphor, polidocanol, lidocain, tetracain, mepivacain, benzocain, prilocain, bupivacain and their hydrochlorides and pharmaceutical/cosmetic acceptable salts.

6. The method of claim 1, wherein the dermal patch and/or the hydrogel patch further contains aloe barbadensis leaf extract and/or polidocanol.

7. The method of claim 1, wherein the dermal patch and/or the hydrogel patch contains panthenol and aloe barbadensis leaf extract.

8. The method of claim 1, wherein the dermal patch and/or the hydrogel patch contains panthenol, aloe barbadensis leaf extract and polidocanol.

9. The method of claim 1, wherein the hydrogel patch comprises a hydrogel sheet which contains at least 0.10 wt.-% panthenol and said hydrogel sheet optionally contains at least 0.10 wt.-% aloe barbadensis leaf extract.

10. The method of claim 1, wherein the dermal patch comprises an active sheet which contains at least 0.20 wt.-% panthenol, and said active sheet optionally contains at least 0.20 wt.-% aloe barbadensis leaf extract.

11. The method of claim 1, wherein the method comprises applying the hydrogel patch to a person's skin, then removing the hydrogel patch after 5 minutes to 24 hours, and then applying the dermal patch to the person's skin approximately at the same position where the hydrogel patch was applied.

12. The method of claim 1, wherein the method is for maintaining the color saturation of a tattoo.

13. The method of claim 1, wherein the dermal patch comprises an active sheet, wherein the active sheet contains at least a polymeric binder, an emulsifier, panthenol, aloe barbadensis leaf extract, and a surfactant.

14. The method of claim 1, wherein the hydrogel patch comprises a hydrogel sheet, wherein the hydrogel sheet contains at least water, a gelling agent, a thickener, an emulsifier, a preservative and/or a moisturizer, panthenol, and aloe barbadensis leaf extract.

15. The method of claim 1, comprising the step of applying the dermal patch and the hydrogel patch to skin after tattooing, wherein the dermal patch and/or the hydrogel patch contains at least one active agent selected from the group consisting of vulnerary agents, anti-inflammatory agents, soothing agents, cooling agents and analgesic agents.

* * * * *

UNITED STATES PATENT AND TRADEMARK OFFICE
CERTIFICATE OF CORRECTION

PATENT NO. : 10,420,713 B2
APPLICATION NO. : 15/304284
DATED : September 24, 2019
INVENTOR(S) : Grasl et al.

It is certified that error appears in the above-identified patent and that said Letters Patent is hereby corrected as shown below:

In the Claims

Column 12, Lines 33-37, Claim 1 should be: -- A method for use of a dermal patch and a hydrogel patch for the post-treatment of skin after tattooing, comprising the step of applying the dermal patch and the hydrogel patch to skin after tattooing wherein the dermal patch and/or the hydrogel patch contains panthenol. --

Signed and Sealed this
Twelfth Day of November, 2019

Andrei Iancu
*Director of the United States Patent and Trademark Office*